United States Patent [19]

Gaylord

[11] Patent Number: 5,795,316
[45] Date of Patent: Aug. 18, 1998

[54] ANKLE STABILIZING APPLIANCE FOR RESTRICTING INVERSION AND EVERSION OF THE FOOT

[75] Inventor: Eric Lee Gaylord, Matthews, N.C.

[73] Assignee: Medical Specialties, Inc., Charlotte, N.C.

[21] Appl. No.: 883,619

[22] Filed: Jun. 26, 1997

[51] Int. Cl.$^6$ ........................................................ A61F 5/00
[52] U.S. Cl. ........................................ 602/27; 602/65
[58] Field of Search ............................... 602/5, 23, 27, 602/61, 63, 65; 128/882

[56] References Cited

U.S. PATENT DOCUMENTS

| | | | |
|---|---|---|---|
| 3,073,305 | 1/1963 | Biggs, Jr. et al. | 602/65 |
| 4,085,746 | 4/1978 | Castiglia | 602/65 |
| 4,313,433 | 2/1982 | Cramer | 602/27 |
| 4,495,942 | 1/1985 | Palumbo | 602/27 |
| 4,527,556 | 7/1985 | Nelson . | |
| 4,724,847 | 2/1988 | Nelson | 602/27 |
| 4,727,863 | 3/1988 | Nelson . | |
| 4,729,370 | 3/1988 | Kallassy | 602/65 |
| 4,762,123 | 8/1988 | Dedo . | |
| 4,825,856 | 5/1989 | Nelson | 602/27 |
| 4,844,058 | 7/1989 | Vogelbach | 602/27 |
| 4,878,504 | 11/1989 | Nelson | 602/27 |
| 4,878,505 | 11/1989 | Thanner | 602/65 X |
| 4,962,768 | 10/1990 | Stromgren et al. | 602/27 |
| 4,998,537 | 3/1991 | Rau | 602/27 |
| 5,000,195 | 3/1991 | Neal | 602/27 |
| 5,050,620 | 9/1991 | Cooper | 602/27 |
| 5,067,486 | 11/1991 | Hely . | |
| 5,139,479 | 8/1992 | Peters | 602/27 |
| 5,217,431 | 6/1993 | Toronto et al. . | |
| 5,393,303 | 2/1995 | Shiono | 602/27 |
| 5,620,413 | 4/1997 | Olson | 602/27 X |
| 5,676,641 | 10/1997 | Arensdorf et al. | 602/27 |

*Primary Examiner*—Linda C. Dvorak
*Attorney, Agent, or Firm*—Bell Seltzer Intellectual Property Law Group of Alston & Bird, LLP

[57] ABSTRACT

An ankle stabilizing appliance for restricting inversion and eversion of the foot while allowing flexion and dorsiflexion is described. The appliance includes a boot-like body member and a pair of stabilizing straps which extend in opposite directions toward the front of the body member. Each of the stabilizing straps is adapted to extend across and under the foot of the wearer, and then upwardly to a releasable attachment point on the side of the body member. A first fastener of a unidirectional fastener pair is positioned on a lower portion of the body member, in a position where it will be positioned beneath the calcaneus of a wearer when the device is worn. A mating fastener is positioned on a central portion of one of the stabilizing straps so that when the strap is wrapped across and under the foot of the wearer, the mating fasteners are secured together, and the unidirectional fastener protects against relative movement between the body member and the strap. In addition, the unidirectional fastener pair enables the stabilizing strap to be cinched tighter while the device is being worn, and protects the strap from having a tendency to loosen during wear. A pair of asymmetric malleoli pads are also provided on the body member such that they abut the wearer's malleoli and prevent the device from collapsing during wear as a result of downward forces caused by the securement of the stabilizing straps. The body member also includes one or more binding straps which are adapted to be looped around the ankle of the wearer, in an overlying relationship to the stabilizing straps.

24 Claims, 6 Drawing Sheets

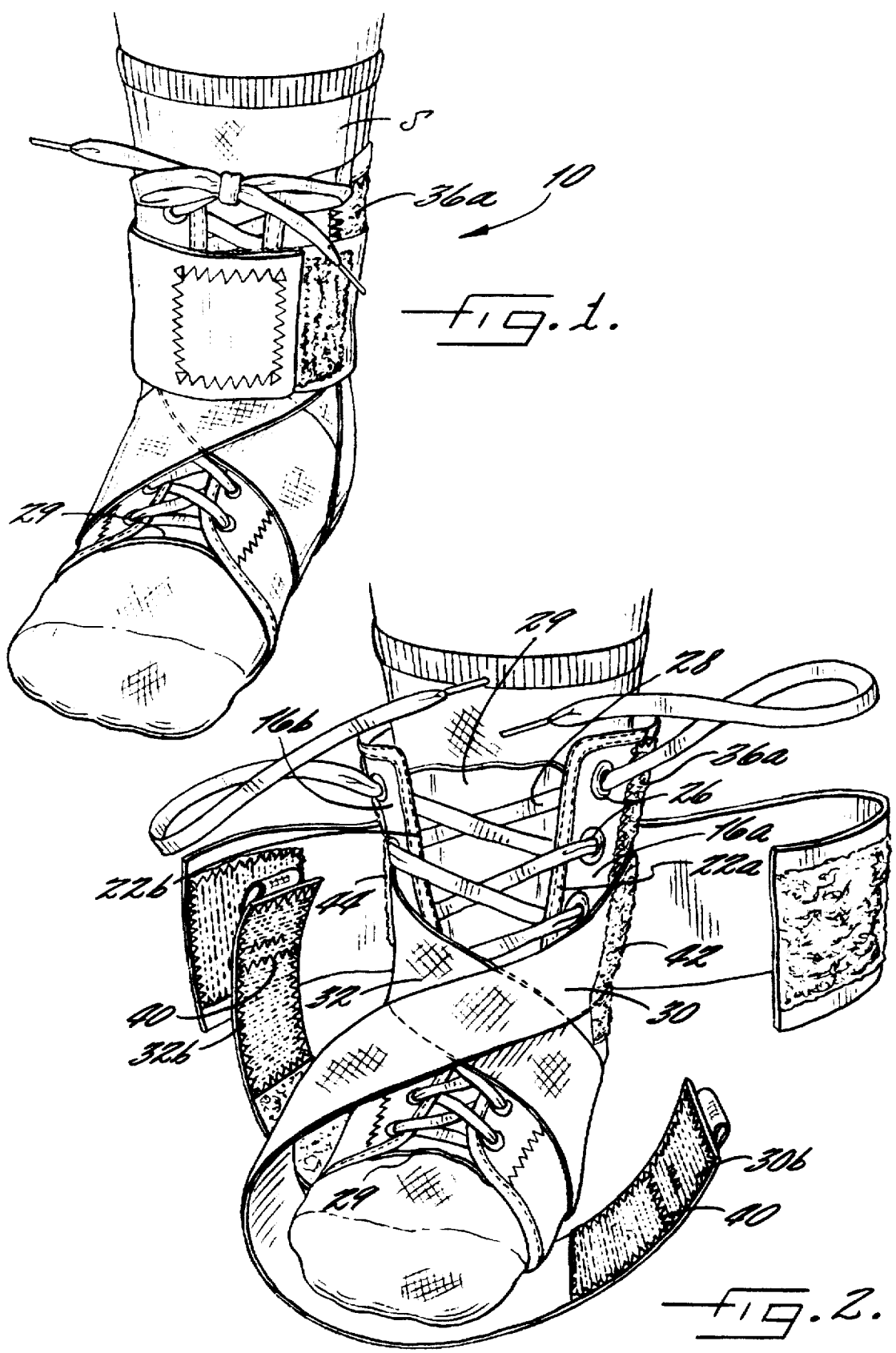

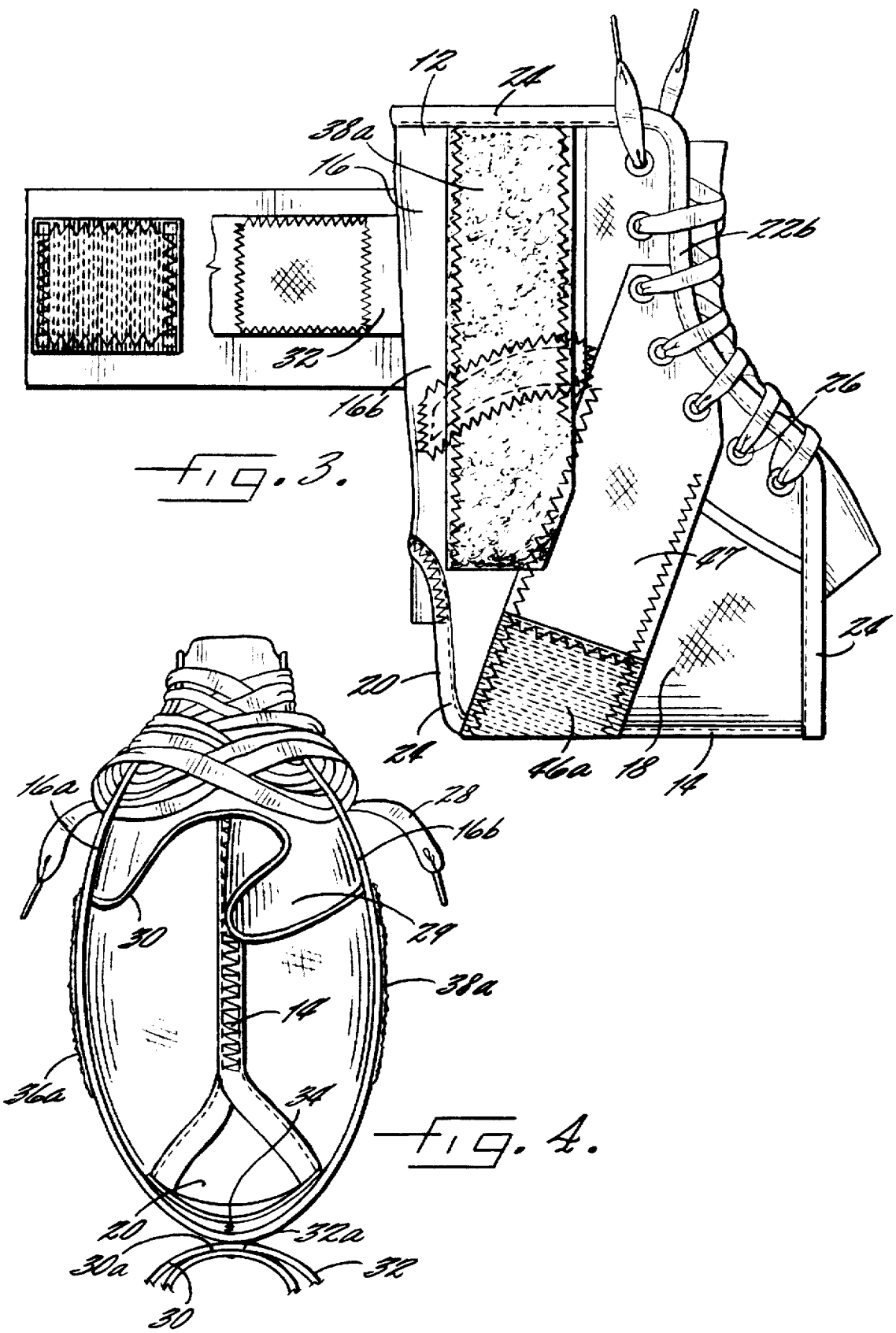

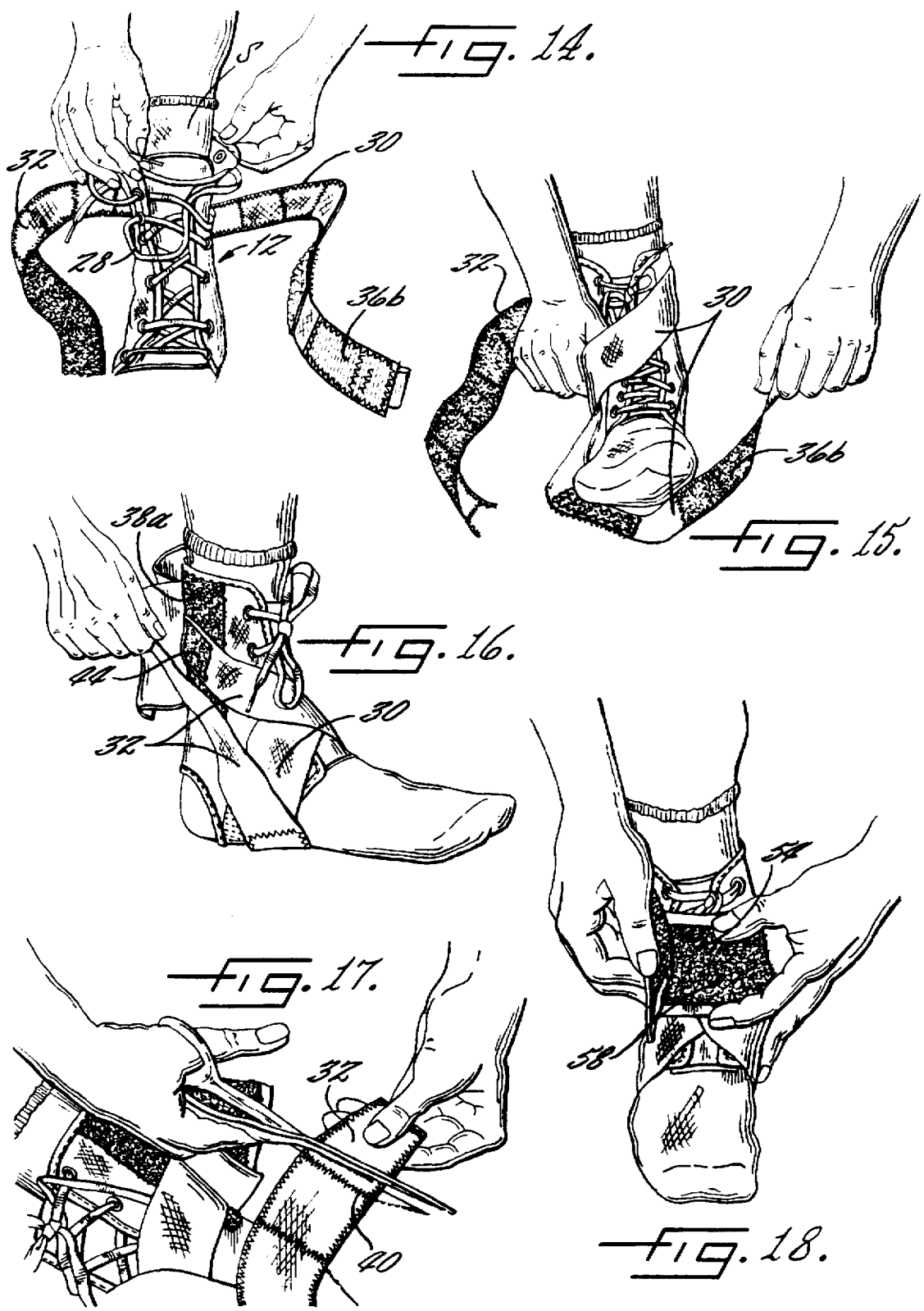

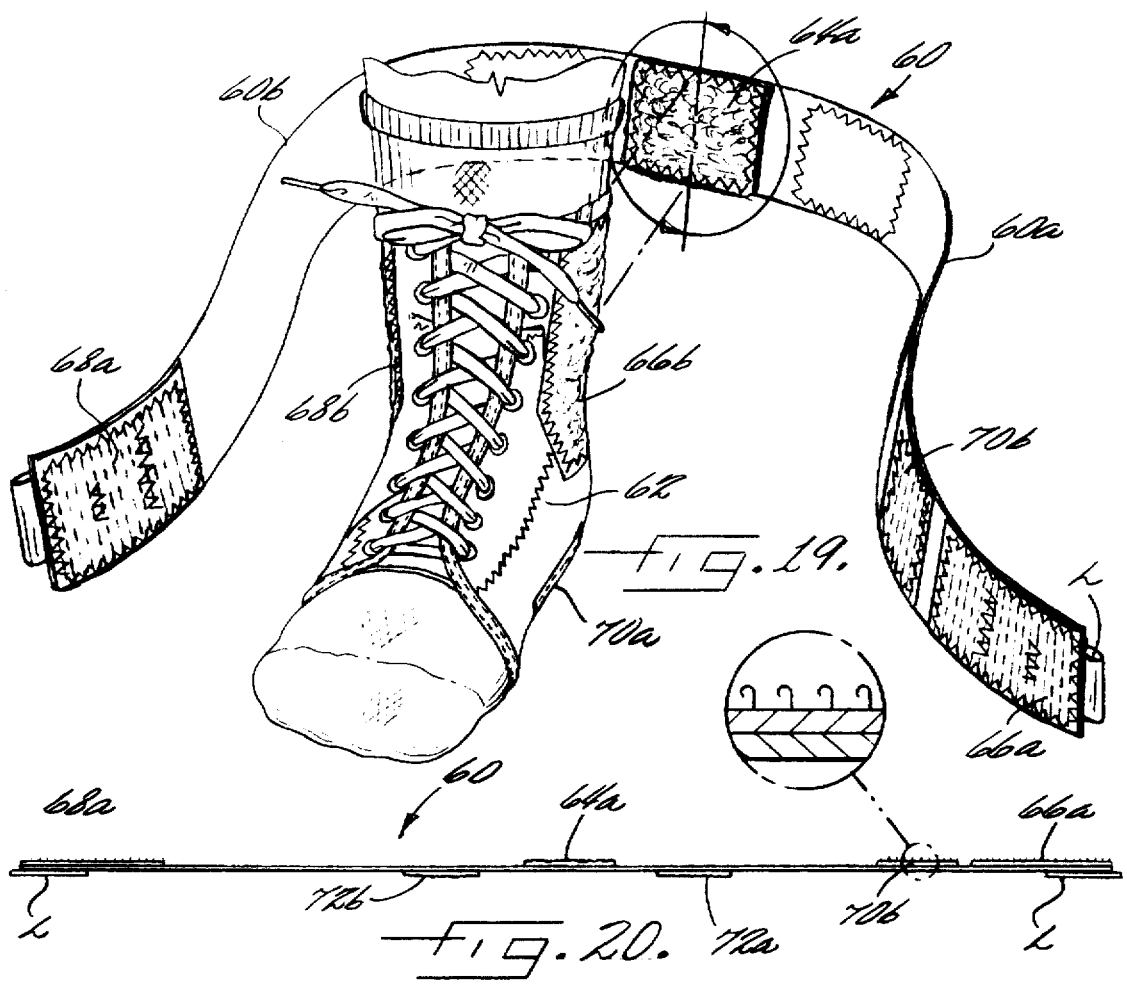
FIG. 19.
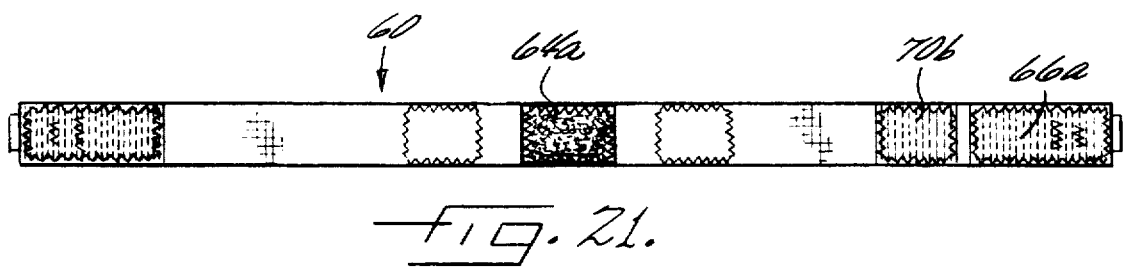
FIG. 20.
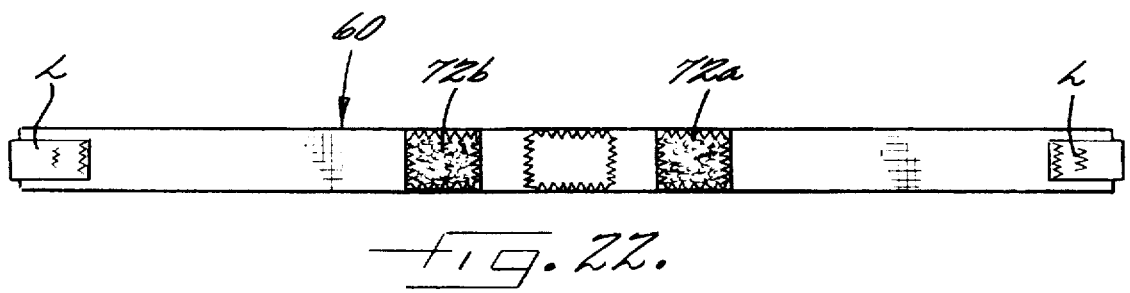
FIG. 21.
FIG. 22.

ANKLE STABILIZING APPLIANCE FOR RESTRICTING INVERSION AND EVERSION OF THE FOOT

FIELD OF THE INVENTION

The invention generally relates to an ankle stabilizing appliance and more specifically, to an ankle stabilizing appliance for minimizing inversion and eversion of the foot, without unduly restricting flexion and dorsiflexion.

BACKGROUND OF THE INVENTION

Participants in athletics and other similar activities often incur injuries, e.g., as a result of contact with other participants or items of equipment, or as a result of one or more of their body parts assuming an unnatural position during play. Certain regions of an athlete's body tend to be particularly vulnerable to injury during motions typically associated with athletics, such as running, jumping, falling, or the like. For example, a great percentage of sports injuries involve ankles, as these portions of the human body tend to be particularly vulnerable to sprains, fractures, and the like.

Because a large number of ankle injuries occur when the foot is caused to roll inwardly (eversion) or outwardly (inversion) from the leg, many athletes considered to be at risk for ankle injuries have found it beneficial to utilize some form of ankle support during participation in sporting events. One such means of providing supplemental ankle support is taping, where the athlete or trainer winds athletic tape around the athlete's ankle in order to limit the motion thereof. While this method has been found to stabilize the ankle against undesired motion to a degree, it can have a number of drawbacks. For one, because the tape is wound circumferentially around the ankle, essentially all motions of the ankle, both desirable and undesirable, are restricted, which can thus hinder the athlete's ability to perform. Further, the disuse of certain muscles caused by the binding of the tape can result in reduced muscle conditioning, which can in turn lead to diminished muscle tone and even atrophy of various ankle supporting muscles. In addition, the tape tends to stretch and loosen as the athlete moves, thereby decreasing its effectiveness in supporting the ankle; the loosening also tends to be exacerbated by wetting which occurs from the athlete's perspiration. Furthermore, because removal of the athletic tape tends to be extremely painful if the tape is allowed to contact the hair on an athlete's legs, such athletes are often forced to shave the regions to be taped, which can be aesthetically unappealing.

Other stabilization devices have been employed, with the devices generally being directed to boot-like members which cover the athlete's foot and ankle, and include supplemental straps which are designed to wrap around and stabilize certain areas of the wearer's foot and/or ankle. One such device is described in commonly-assigned U.S. Pat. No. 5,067,486, the disclosure of which is incorporated herein by reference. The stabilizing device of the '486 patent includes a boot-like body member and a pair of stabilizing straps which extend in opposite directions from a rear portion of the body member. Each of the straps is adapted to extend across the top, under the foot of the wearer, and then upwardly to a releasable attachment point on the side of the body member. Another pair of oppositely directed straps is also provided, with the straps being adapted to loop about the ankle of the wearer in an overlying relationship with the stabilizing straps.

It has been found that the majority of ankle sprains are caused by eversion and inversion of the foot, with 75-90% of those sprains being attributable to inversion (i.e., rolling outward of the foot.) While the device described in the '486 patent has been found to reduce the incidence of injuries resulting from inversion and eversion, it has been found that the stabilizing straps may still allow some movement of the distal end of the calcaneus, and some undesirable movement of the ankle may be allowed through movement of the boot itself relative to the wearer's foot (e.g., through collapse of the upper ankle encircling portion of the boot caused by the downward pressure of the stabilizing straps.) In addition, because the device cannot be adjusted specifically for the left or right foot, it can be somewhat difficult to obtain a foot specific fit, thereby diminishing the ability of the device to isolate the ankle from all undesirable movement.

Thus, a need exists for an ankle stabilizing device which effectively minimizes the occurrence of ankle sprains, without reducing the athlete's performance.

SUMMARY

It is therefore an object of the present invention to provide an ankle stabilizing appliance which effectively minimizes the occurrence of ankle sprains without unduly restricting the desirable motions of the ankle.

It is also an object of the invention to provide an ankle stabilizing appliance which maintains effective support of the wearer's ankle throughout its use.

It is a further object of the present invention to provide an ankle stabilizing appliance which can be easily applied by the wearer, and can be tightened with ease while in position on the wearer's foot.

The above and other objects and advantages are achieved in accordance with the present invention by the provision of an ankle stabilizing appliance which effectively minimizes inversion and eversion of the foot, while permitting flexion and dorsiflexion thereof. This appliance desirably has a substantially L-shaped boot-like body member formed from a flexible, substantially non-elastic material, which is adapted to receive at least the ankle and a rear foot portion of a foot. The body member desirably has an ankle portion adapted to overlie the sides and rear of the ankle of the wearer, and a vertical length which is sufficiently large that the body member overlies the malleoli when positioned on a wearer's foot. The body member is also desirably sized and shaped such that it extends beneath the calcaneus when the device is worn. The body member desirably includes opposing laterally spaced apart front edges extending along the length of the ankle portion and at least a portion of the foot portion. In a preferred form of the invention, the front edges extend along substantially the entire length of the ankle and foot portions of the body member in order that the body member is open and thus adjustable along substantially its entire length.

The ankle portion of the body member defines an inside panel for covering the inside of the ankle and an outside panel on the opposite side for covering the outside of the ankle. The ankle portion also defines a rear edge portion which extends vertically between the inside and outside panels and thus covers the Achilles tendon region of a wearer's foot when the device is worn. The body member also desirably includes a connector for drawing the front edges of the body member together so as to permit the body member to be secured snugly about a wearer's foot. This connector can be of any conventional type, including, but not limited to lacing and eyelet combinations, buckles, straps, and the like.

The device also desirably includes a pair of elongate substantially non-elastic stabilizing straps, each of which is operatively associated with a rear portion of the ankle portion. The straps extend laterally in opposite directions such that one strap defines an inside strap extending from the position where its end is secured toward the inside panel and the second strap defines an outside strap extending from the position where its end is secured toward the outside panel. These straps can be integrally formed from a single piece of strap material or can be formed individually from separate pieces of strap material. Also, the stabilizing strap(s) can be permanently or releasably attached to the boot-like body member, within the scope of the instant invention.

A first fastener of a first pair of mating fasteners is attached to the inside panel of the ankle portion while the second fastener of the pair is attached to the free end of the inside strap. Additionally, a first fastener of a second pair of mating fasteners is attached to the outside panel of the ankle portion while the second of that fastener pair is attached to the free end of the outside strap. In this way, the stabilizing straps can be secured in their operative positions by securement of the mating fasteners in a manner which will be described further herein.

In a preferred embodiment of the invention, the stabilizing straps are attached at or near the rear edge portion of the ankle portion at an elevation above the malleoli of the wearer, such that when the straps are secured in their operative position, effective restraint from inversion and eversion of the ankle can be obtained, while flexion and dorsiflexion are permitted.

A third pair of mating fasteners is also provided, with this pair desirably being of the unidirectional variety. Particularly preferred is a unidirectional fastener pair of the molded unidirectional hook and loop variety commonly sold by VELCRO®, Inc. Such fasteners are commonly used in the automotive industry for the attachment of dashboards in vehicles, because such fasteners provide little resistance to relative movement between the fasteners in one direction (i.e., the direction of dashboard insertion) while substantially eliminating relative movement in other directions. A first fastener of the third fastener pair is desirably provided on an underside of the body member substantially corresponding to at least a portion of a wearer's calcaneus, while the mating fastener is desirably provided on a central portion of one of the stabilizing strap of the strap pair which is adapted to be secured around the wearer's foot first (as will be discussed below.) It is particularly preferred that the unidirectional fastener be positioned on the body member and strap, respectively, such that the direction of permitted relative movement extends laterally in a direction toward the ankle portion panel to which the unidirectional fastener bearing stabilizing strap is secured. In this way, the unidirectional fasteners will permit ready tightening of the device while it is on the foot with the fasteners in their secured form, yet the strap and body member are protected from relative movement which loosens the stabilizing strap while the fasteners of the pair are secured together.

In a preferred form of the invention, one of the fasteners forming the third fastener pair is secured to a central portion of the inside strap. After securing of the body member on the wearer's foot, the inside strap is then brought across the inside panel of the ankle portion, over the top of the wearer's foot, downwardly across the outside of the wearer's foot, and under the wearer's foot, where the third fastener pair is secured together such that the inside strap is positioned securely beneath at least a portion of the calcaneus of the wearer's foot. The inside strap is then brought upwardly so that the free end thereof can be attached to the inside panel of the ankle portion of the body member by way of the second fastener pair being secured together.

The second stabilizing strap (i.e., the outside strap) is then wrapped around the wearer's foot by bringing it across the outside panel, over top of the wearer's foot, downwardly across the inside of the wearer's foot, under the wearer's foot, and then upwardly so that the free end thereof can be secured to the outside panel of the ankle portion of the body member by way of the first mating fastener pair being secured together. Though for purposes of illustration the inside strap is described as being wrapped around the foot first, and thus utilizes the third fastener pair to secure it proximate the wearer's calcaneus, it is noted the outside strap can be adapted to be wrapped around the foot first, in which case a fastener of the third fastener pair would be provided on a central portion of the outside strap rather than the inside strap.

In another form of the instant invention, a fourth pair of mating fasteners is provided such that when the second stabilizing strap is secured following the first stabilizing strap in the manner described above, the fourth fastener pair is positioned between the first and second straps. In other words, one of the fasteners is secured to the outside surface of one of the stabilizing straps, while the other is secured to the underside surface of the opposite stabilizing strap. In a preferred form of this embodiment, the mating fourth fasteners are positioned so as to be located beneath the calcaneous of the foot when the device is worn. In a particularly preferred form of the invention, the fourth fastener pair is in a stacked relationship with the third fastener pair when worn, and the fastener pair is of the above-described unidirectional variety, so that the strap can be cinched in the direction which tightens it about a wearer's foot.

In a preferred form of the invention, the appliance also includes a pair of asymmetrical malleoli pads. A first of the pads is positioned on said inside panel of the body member such that it extends over top of a wearer's inside malleolus, while the second of the malleoli pad pair is positioned on said outside panel of said body at a position where it will extend above the outside malleolus of the wearer. The pads are asymmetrical, in order to accommodate the differential prominence of the inside (medial) and outside (lateral) malleoli, such that when the device is worn, the pads support the upper portion of the body member from having a tendency to collapse as a result of the downward pressure caused by the securement of the stabilizing straps. In addition, the pad adapted to contact the outside malleolus is desirably thicker and taller than that of the inside malleolus. In one form of the invention, the malleoli pads are secured on the body member such that the inside malleolus pad is slightly higher than the outside pad, to accommodate the slight differential in height and shape usually present between the prominent portions of the inside and outside malleoli. In another preferred embodiment of the invention, a pair of substantially symmetrical pockets are provided on the inside and outside panels of the body member, with each of the pockets being adapted to selectively receive one of the differently shaped inside and outside malleolus pads. Because the inside malleolus pad is thinner and shorter than the outside malleolus pad, it is smaller than the pockets, and thus has a tendency to be pushed upwardly to the upper end of the pocket when the appliance is positioned on a wearer's foot. In this way, the pads can be positioned by the wearer such that the wearer can selectively configure the appliance for wear on either of the right or left feet.

The appliance also preferably includes at least one binding strap which is fixed to said ankle portion and adapted to be wrapped and secured circumferentially around a wearer's ankle. In a preferred form of the invention, the binding strap is positioned at a height on the appliance so that it overlies portions of the stabilizing straps and the lacing, to provide support thereto. Though referred to as a binding strap, it is noted that the strap can comprise a plurality of straps which cooperate to form a circumferentially extending strap around a wearer's ankle, or can be provided as a single strap having sufficient length to extend circumferentially around the wearer's ankle region. Further, the binding strap(s) can be secured either permanently or releasably to the boot-like body member, or in the releasable stabilizing strap embodiment, directly to the stabilizing strap itself.

Because of the unidirectional fastener pair(s), the invention can be readily re-tightened during wear, without requiring that the laces be loosened and then retightened. More particularly, the appliance may be re-tightened by releasing the outer binding strap, releasing the first and/or second fastener pairs and pulling on the free end of the stabilizing straps, and then reconnecting the stabilizing straps and binding strap. The unidirectional fastener pair, which is desirably positioned on the strap and body member such that the direction of relative movement is the direction which causes strap tightening, thus does not have to be separated, rather it can just be cinched tighter on the wearer's foot while still in its secured condition.

BRIEF DESCRIPTION OF THE DRAWINGS

Some of the objects and advantages of the present invention having been stated, others will appear as the description proceeds, when taken in conjunction with the drawings, in which:

FIG. 1 is a perspective view of an ankle stabilizing appliance according to the present invention as it appears when positioned on a foot of a wearer;

FIG. 2 is a perspective view of the ankle stabilizing appliance of FIG. 1, as it appears when mating fasteners are released from each other;

FIG. 3 is a side elevational view of an appliance according to the instant invention;

FIG. 4 is a top plan view of an appliance according to the instant invention, as viewed looking down into the appliance;

FIGS. 14-18 are perspective views illustrating the steps involved in applying an appliance according to the instant invention to a wearer's foot;

FIG. 19 is a perspective view of an embodiment of the invention utilizing a releasably attached strap which forms the first and second stabilizing straps;

FIG. 20 is a side elevational view of the releasable strap of FIG. 19, with a portion of one of the fasteners shown greatly enlarged;

FIG. 21 is a plan view of the upper side of the strap of FIG. 20; and

FIG. 22 is a plan view of the lower side of the strap of FIG. 20.

DETAILED DESCRIPTION

Figure 5:
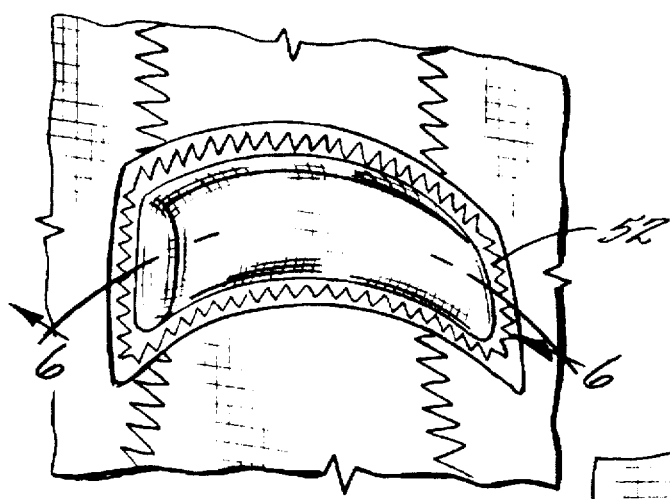
FIG. 5 is a perspective view of one of the malleoli pads positioned on the interior of an appliance according to the instant invention.
Figure 6:
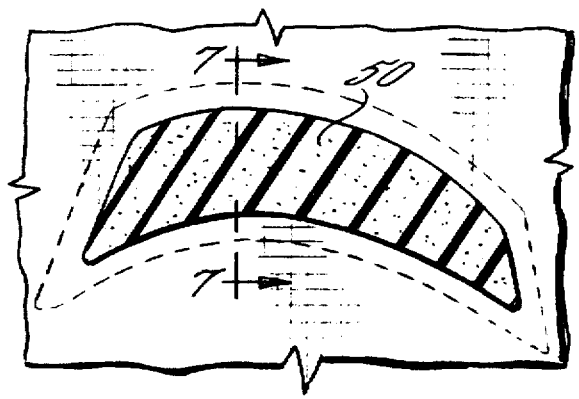
FIG. 6 is a perspective view of the malleolus pad illustrated in FIG. 5, as it appears with the cover removed.
Figure 7:
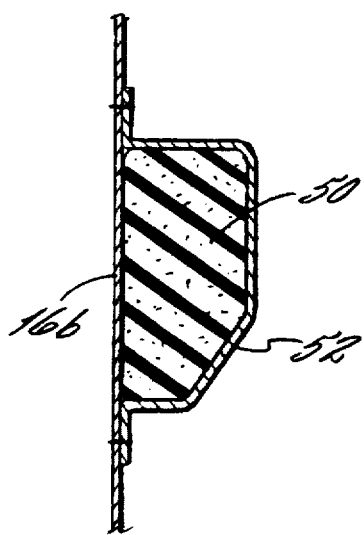
FIG. 7 is a cross-sectional view of the malleolus pad of FIG. 6, as taken along line 7—7 of that figure.
Figure 8:
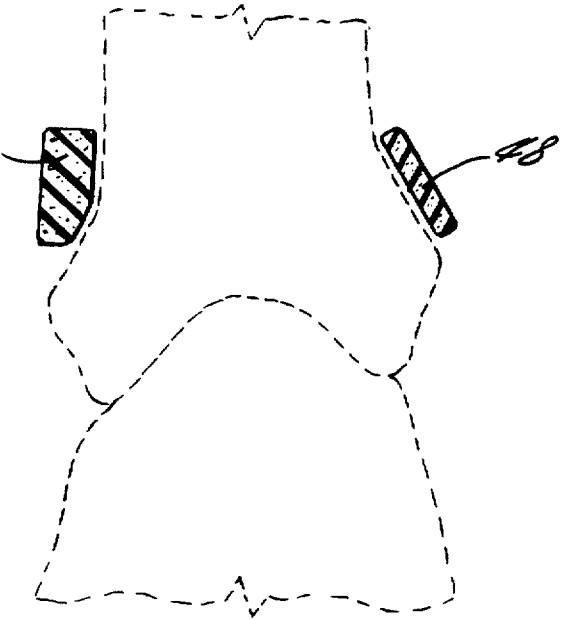
FIG. 8 is a cross-sectional view of the bones of a wearer's foot, illustrating the positioning of the malleoli pads when the appliance is properly worn by the wearer.
Figure 9:
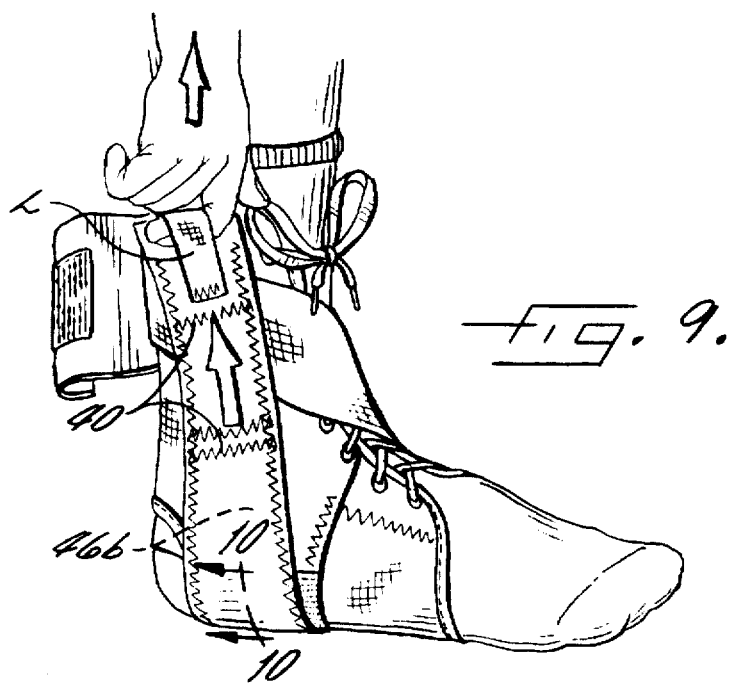
FIG. 9 is a perspective view of a wearer donning the appliance of the instant invention.

The ankle stabilizing appliance of the present invention is generally indicated at 10. As illustrated, the appliance 10 is preferably worn over an athletic sock S, though an underlying sock is not required. The appliance 10 is designed to be configurable for either the right or left foot; therefore FIG. 1 illustrates a right foot specific device as it appears when worn on a wearer's right foot. A left foot specific device would be a mirror-image version of the one illustrated in FIG. 1, as will be understood by those having ordinary skill in the art.

The appliance 10 includes a boot-like body member 12 which is preferably fabricated from a flexible substantially non-elastic fabric material. In a preferred embodiment of the invention, the substantially non-elastic material is a woven ballistic nylon fabric, as such fabrics have been found to be light weight, while providing a high degree of strength and durability. In addition, such fabrics are generally relatively thin, which is particularly desirable when the wearer utilizes the device inside a shoe (not shown). The sheet of material is desirably folded and seamed to form a substantially L-shaped configuration for covering at least lower and rear portions of a wearer's foot and ankle. In the illustrated embodiment of the invention, the seam 14 formed during the above-noted seaming operation is positioned so that it extends along a lower portion of a wearer's foot; however, it is noted that the seam could be positioned along other portions of the device, such as to extend along the Achilles tendon region of a wearer's foot.

The boot-like body member 12 preferably defines an upper ankle portion 16 which is adapted to overlie both sides and the rear of the ankle of the wearer, and a lower foot portion 18 adapted to extend under the foot of the wearer. More particularly, the ankle portion 16 desirably includes upstanding inside and outside panels 16a and 16b, respectively, and the foot portion 18 is disposed between the lower ends of the upstanding panels 16a and 16b. The ankle portion 16 is adapted to be of sufficient length so as to extend vertically above the malleoli of the wearer. A cutout 20 can be provided at a rear portion of the foot portion 18 of the body member 12, for receiving the heel portion of the wearer's foot.

The two upstanding panels 16a, 16b of the body member 12 also define opposing laterally spaced apart front edges 22a, 22b, which extend along at least a portion of the front of the ankle portion 16. In a preferred form of the invention, the edges 22a, 22b also extend along the foot portion 18, such that the body member 12 is adjustable substantially along its entire length. These front edges 22a, 22b are desirably curved in nature so that when in place, the body member 12 substantially conforms to the front of the shin and the top of the foot of the wearer.

An overedge binding strip 24 can be sewn along the front edges 22a, 22b, as well as along the edges which define the heel opening 20, the top of the inside and outside panels 16a, 16b, and the front of the foot portion 18 in order to provide non-raveling edges and a finished appearance to the appliance. Also, a connector is desirably provided for joining the two front edges 22a, 22b together to secure the body member 12 on a wearer's foot. In a preferred form of the invention, the connector is in the form of plurality of eyelets 26 which are placed along the length of each of the opposing front edges 22a, 22b, and through which a flexible strand of lacing 28 is threaded in a conventional manner to thereby interconnect the edges and permit them to be drawn toward each other to cause the body member 12 to be tightly secured about the ankle and rear portion of the foot of the wearer.

A tongue 29, as best seen in FIG. 4, is desirably secured between the opposing laterally spaced apart front edges 22a, 22b of the body member 12. The tongue 29, which preferably is composed of an elastic padded material such as a foam backed knit fabric, desirably assists in the securement of the body member 12 to a wearer's foot, and provides padding between the lacing 28 and the wearer's foot.

The device 10 also desirably includes a pair of elongate substantially non-elastic stabilizing straps 30, 32 which are attached to the body member 12 such that each strap includes a first end effectively secured to the ankle portion 16 at or near a rear portion thereof, and an opposite free end. The stabilizing straps can be secured to the ankle portion 16 in a releasable manner (e.g., by hook and loop fasteners) or in a permanent manner (e.g., by sewing.) In the illustrated embodiment, the stabilizing straps 30, 32 are secured to the ankle portion 16 by sewing along seam line 34. The stabilizing straps 30, 32 can be formed individually or, as in the form of the invention shown in FIG. 4, formed from a single piece of material which is seamed along a central portion thereof to the body member 12, to thereby form the two stabilizing straps 30, 32. The outside strap 32 has a fixed first end 32a and a free opposite end 32b, and the inside strap 30 has a fixed first end 30a and an opposite free end 30b. The stabilizing straps 30, 32 are desirably attached at or near the rear portion of the ankle portion 16 at an elevation which is designed to be located above the malleoli of the wearer, for reasons which will be discussed further herein.

As illustrated, the inside strap 30 extends laterally from the rear of the ankle portion 16 toward the inside panel 16a, while the outside strap 32 extends laterally from the rear of the ankle portion toward the outside panel 16b. The straps are preferably formed from a strapping-type material such as a ballistic nylon fabric, so as to be strong without being very thick, in order that they do not cause discomfort to the bottom of the wearer's foot when the device is positioned on a wearer's foot in its operable position. In a preferred embodiment of the invention, the stabilizing straps 30, 32 are attached at or near the rear portion of the ankle portion 16 at an elevation above the malleoli of the wearer, such that effective restraint from inversion and eversion of the ankle can be obtained, while flexion and dorsiflexion are permitted.

For the purpose of securing the stabilizing straps about the foot of the wearer in the manner described below, there is provided a first mating fastener pair 36 with a first fastener 36a of the pair being attached to the outer face of the inside panel 16a and the other fastener 36b being attached to the free end 30b of the inside strap 30, while a first fastener 38a of a second fastener pair 38 is attached to the outer face of the outside panel 16b, and the second fastener 38b is attached to the free end 32b of the outside strap 32. In a preferred embodiment of the invention, the mating fastener pairs 36, 38 are in the form of hook and loop fasteners of the type sold under the tradename VELCRO®.

The fasteners which are attached to the inside 16a and outside 16b panels of the body member 12 desirably extend vertically from an upper portion of the upper ankle portion 16 downwardly toward the foot portion. The fasteners which are attached to the free ends 30b, 32b of the straps 30, 32, respectively, are desirably elongate, as best seen in FIG. 2, and preferably include intermediate transverse seam lines 40 which permit the straps to be shortened by cutting along the outside of one of the seam lines in the manner shown in FIG. 17. The transverse seam line which is closest to the cut will ensure the attachment of the fastener to the strap material after such cutting, and prevents raveling of the strap material.

As desired, an additional piece of fastener material 42 can be attached to the outside of the inside stabilizing strap 30 at a location near the fixed end 30a of the strap. This strip is preferably of the same type, e.g., either loop or hook, as the piece of fastener material 36a located on the inside panel 16a, and is located at such a position that when the inside strap is in its operable position (discussed below), the additional strip 42 overlies the fastener 36a. In this way, a greater degree of adjustability is provided due to the greater dimensional area covered by the fastener material. A similar fastener 44 can also be attached to the outside of the outer strap 32 for engaging the fastener 38b at the free end 32b of that strap.

A third pair of mating fasteners 46 is also provided, with this pair desirably being of the unidirectional variety. Particularly preferred is a unidirectional fastener pair of the molded unidirectional hook and loop variety commonly sold by VELCRO®, Inc. Such fasteners typically have a first fastener piece having a plurality of hooks thereon, and a second fastener piece with a plurality of filament loops thereon, in the manner of multidirectional conventional hook and loop fasteners. Unlike their multidirectional counterparts, however, which generally do not allow for any relative movement between fastener pieces, the hook fastener piece of the unidirectional fastener pair has all of its hooks curved in a common, and preferably a single same, direction. In addition, the hooks are generally manufactured to be somewhat thicker and stiffer than those typically employed in the multi-directional fastener varieties, in order that the hooks retain their common direction of curve during use. Because all of the hooks are curved in a common direction, relative movement is allowed when the loop fastener piece is moved laterally with respect to the hook fastener piece in the direction of the hook curve. However, the fastener pieces are restrained from relative movement in other directions.

A first fastener 46a of the third fastener pair 46 is desirably provided on an underside of the body member 12 substantially corresponding to at least a portion of a wearer's calcaneus, while the mating fastener 46b is desirably provided on a central portion of the stabilizing strap of the strap pair which is adapted to be secured around the wearer's foot first (as will be discussed below.) As illustrated in FIG. 3, the fastener 46a can be secured to a piece of strapping material 47, which assists in maintaining the fastener in a smooth condition underneath the wearer's foot. Alternatively, the fastener 46a can be sewn or otherwise secured directly to the boot-like body member without the strapping material 47. The first fastener 46a is desirably positioned on the underside of the body member 12 with the direction of permitted relative movement extending laterally in a direction toward the ankle portion to which the unidirectional fastener bearing stabilizing strap is secured. In this way, the relative movement is allowed in a direction which serves to tighten the device on a wearer's foot, in a manner discussed further below.

Figure 11:
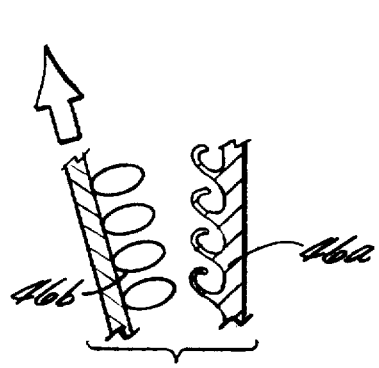
FIGS. 10-13 are cross-sectional views of a form of unidirectional fastener useful in the instant invention, illustrating the interaction of the fasteners when the pieces are moved relative to each other in the directions indicated by the arrows.
Figure 10:
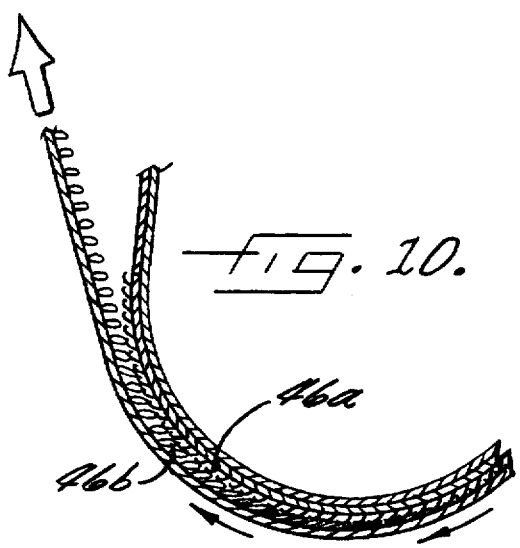
Figure 12:
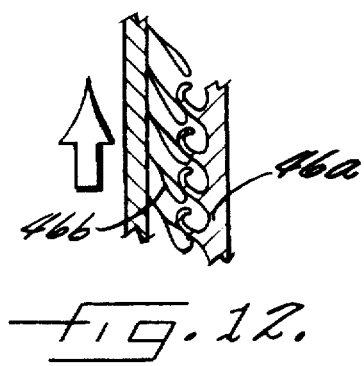
Figure 13:
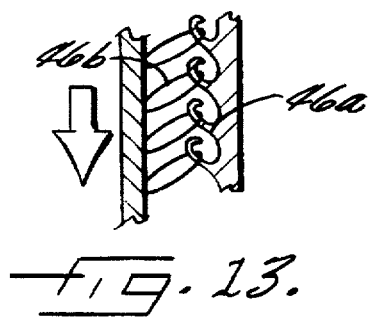

The operation of the unidirectional fastener is shown in FIGS. 10–13. As shown in FIGS. 10–12, relative motion of the individual fasteners 46a, 46b in a first direction causes the loops on one fastener to disengage from the hooks on the other fastener because substantially all of the hooks are curved in a single same direction, and as a result, the fasteners can be separated altogether (FIG. 11) or they may stay together while one fastener moves relative to the other such that tightening of the fastener is allowed (FIG. 12). Upon release of the force in the one direction which allows relative movement of the fasteners, the unidirectional hooks of the fastener 46a again engage the loops of the other fastener 46b, thereby securing the fastener together.

In a preferred form of the invention, the unidirectional fastener pair 46 is positioned on the stabilizing strap 32 and body member 12 such that the direction of relative movement which is allowed between the fasteners 46a, 46b is in the direction which causes tightening of the appliance on a wearer's foot; in other words, in the case of hook and loop fasteners, the hooks are desirably curved toward the panel to which the strap bearing the mating unidirectional fastener is adapted to be releasably attached. In this way tightening of the device can readily be had without resort to entire disengagement the stabilizing strap. Further, although in the illustrated embodiment of the invention, the hook fastener is secured to the body member 12 and the loop fastener is secured to the strap 32, it is noted that these could be reversed, such that the hook fastener is on the strap 32 and the loop fastener is on the underside of the body member. In this case, the hooks are desirably positioned on the strap such that they curve in a direction away from the panel to which the strap bearing the mating unidirectional fastener is adapted to be releasably attached, such that the direction of allowed relative movement is in the direction which causes tightening of the strap.

In a preferred form of operation of the invention, one of the fasteners 46b forming the third fastener pair 46 is secured to a central portion of the outside strap 32. After securing of the body member 12 on the wearer's foot, the outside strap 32 is then brought across the outside panel 16b of the ankle portion 16, over the top of the wearer's foot, downwardly across the inside of the wearer's foot, and under the wearer's foot, where the third fastener pair 46 is secured together such that the outside strap is positioned securely beneath at least a portion of the calcaneus of the wearer's foot. The outside strap 32 is then brought upwardly so that the fastener 38b on the free end 32b thereof can be attached to its mating fastener 38a and/or the additional fastener 42 located on the outside panel of the ankle portion.

The second stabilizing strap, which in the illustrated embodiment is the inside strap 30, is then wrapped around the wearer's foot by bringing it across the inside panel 16a, over top of the wearer's foot, downwardly across the outside of the wearer's foot, under the wearer's foot, and then upwardly so that the fastener 36a on the free end 30b thereof can be secured to the mating fastener 36b on proximate the fixed end 30a of the strap and/or the fastener 38 located on the outside panel 16b of the ankle portion 16 of the body member 12. Though for purposes of illustration the outside strap 32 is described as being wrapped around the foot first, and thus the unidirectional fastener pair 46 is used to secure it proximate the wearer's calcaneus, it is noted the inside strap 30 could be adapted to be wrapped around the foot first, in which case a fastener 46b of the third fastener pair 46 would be provided on a central portion of the inside strap instead.

In a preferred form of the invention, the appliance also includes a pair of asymmetrical malleoli pads. A first of the pads 48 is positioned on said inside panel 16a of the body member 12 such that it extends above and abuts the upper edge of a wearer's inside malleolus, while the second pad 50 of the malleoli pad pair is positioned on the outside panel 16b of said body member at a position where it will extend above and abut the outside malleolus of the wearer. The pads 48, 50 are asymmetrical, in order to accommodate the differential prominence and positioning of the inside and outside malleoli, such that when the device is worn, the pads abut the upper edges of the respective bony prominences to support the upper ankle portion 16 of the body member 12 from having a tendency to collapse as a result of the downward pressure caused by the securement of the stabilizing straps 30, 32. In a preferred form of the invention, the malleoli pad 50 which is positioned to contact the outer malleolus of the wearer is relatively thicker and taller than the malleoli 48 pad positioned to contact the inner malleolus of the wearer, and has a tapered bottom edge for smoothly conforming to the wearer's bone; alternatively, the pad can be substantially rectangular like that of pad 48.

The pads 48, 50 can be secured to the ankle portion 16 of the body member 12 in any conventional manner, such as by positioning it in a pocket formed on either the inner or outer surfaces of the body member by the attachment of an auxiliary lining fabric 52. In one form of the invention, the malleoli pads 48, 50 are secured on the body member 12 such that the inside malleolus pad is slightly higher than the outside pad, to accommodate the slight differential in height and shape usually present between the prominent portions of the inside and outside malleoli. In another preferred embodiment of the invention, a pair of substantially symmetrical pockets are provided on the inside and outside panels of the body member, with each of the pockets being adapted to selectively receive one of the differently shaped inside and outside malleolus pads. In this embodiment, the outer malleolus pad 50 is relatively thicker and taller than the inside malleolus pad 48, with the pockets being large enough to accommodate either of the respective pads. Because of the thinner and smaller size of the inside malleolus pad, it has a tendency to be pushed upwardly in the pocket by way of the pressure of the inside malleolus of a wearer's foot when the appliance is worn. In this way, the pads are operatively positioned such that the inside malleolus pad is relatively higher than the outside malleolus pad, to thereby conform to a wearer's foot. Because the pads can be selectively positioned in the pockets by the wearer, the wearer is enabled to selectively configure the appliance to be worn on either the right or left foot. As will be understood by those of ordinary skill in the art, the lining fabric 52 can be secured to the body member so as to form a substantially closed pocket (as illustrated), or alternatively it can be secured to form an open pocket, wherein the pads will be removable and interchangeable to convert the appliance from one configured for the left foot to one configured for the right foot. In addition, the particular pad used in combination with the device can be selected to accommodate the particular shape of the wearer's malleoli. Also in a preferred form of the invention, the malleoli pads 48, 50 are made of a foam type material such as plastic, which provides cushioning comfort to the wearer as well as support to the body member. The pads 48,50 can be die cut, scissor cut, molded, or made by using any conventional manufacturing methods.

At least one binding strap 54 is provided, which is adapted to be looped about the ankle of the wearer so as to overlie portions of the stabilizing straps 30, 32 and the lacing 28 and the eyelets 26. Preferably, the binding strap 54 is secured to the rear edge portion of the ankle portion 16, and has at least one free end. so that the strap can be wrapped circumferentially about the wearer's ankle to secure the body member 12 more securely to the wearer's foot. Though specifically illustrated as being in the form of a single binding strap which is secured at its central region to the body member 12 to thereby provide two free ends (i.e.. similar to as if two individual straps were used), it is noted that a single strap could be secured at one end and have a single free end which wraps around the wearer's ankle. or a plurality of straps could form the binding strap. The binding strap(s) desirably extends laterally from the rear portion of the ankle portion 16 to overlie at least a portion of the stabilizing straps 30, 32. The free end(s) 56 of the binding strap(s) 54 are secured so that the binding strap encircles the wearer's ankle by way of a pair of mating fasteners 58. This pair of mating fasteners is desirably of the hook and loop fastener variety, though other types of fasteners may be used. In a preferred embodiment of the invention, the binding strap is made from an elastic fabric material, in order that it can closely conform to the wearer's ankle.

As illustrated in FIGS. 14–18, the boot-like body member 12 is adapted to be placed on the appropriate foot of the wearer, preferably over top of an athletic sock S. Once on the foot, the lacing 28 is drawn tight, and secured, such as by tying the lacing into a knot.

The stabilizing straps 30, 32 are then wrapped around the foot. The first strap to be applied can be either the inside strap 30 or the outside strap 32, depending on which has the third fastener 46a located on its central region for matingly attaching to the fastener located on the underside of the body member, proximate the calcaneus of the wearer. For purposes of illustration in these figures, the first strap to be applied is the inside strap 30, which is brought across the inside panel 16a of the ankle portion 16 of the body member 12 and over top of the lacing 28 extending up the opposing front edges 22a, 22b of the body member on the wearer's foot. The inside strap 30 is then extended downwardly across the outside of the wearer's foot and under the wearer's foot, such that the unidirectional mating fastener pair is secured together to secure the strap proximate the calcaneus of the wearer's foot. In this way, the stabilizing strap 30 and the body member 12 are restricted from relative movement except for that in a single predetermined direction. The inside strap 30 is then extended upwardly to the inside panel 16a so that the fastener on the free end 30b can be releasably attached to the fastener on the inside panel 16a of the ankle portion 16 of the body member 12 and/or the fastener on the outside of the strap itself.

The second stabilizing strap, which in the illustrated embodiment comprises the outside strap 32, is then wrapped around the foot by first bringing it across the outside panel and over the top of the lacing 28. The strap 32 is then extended downwardly across the inside of the wearer's foot, and under the wearer's foot. Finally, the strap 32 is extended upwardly past the foot portion so that the free end 32b can be releasably attached to the outside panel 16b of the ankle portion 16 of the body member 12 by securing the fastener 38b to the fastener 38a on the outside panel and/or to the fastener 44 on the outside of the strap itself.

As previously discussed, the stabilizing straps 30, 32 are of sufficient length to allow complete wrapping of the foot in accordance with the above described procedure. Also, the straps 30, 32 are adjustable in length, as depicted in FIG. 17, by cutting the straps 30, 32 at the point just beyond a seam line 40.

To complete the application procedure, the binding strap (s) 54 is/are desirably stretched and engaged in place. More particularly, the binding strap is extended circumferentially around the wearer's leg. and the fourth pair of mating fasteners is secured. preferably such that the binding strap overlies at least a portion of each of the stabilizing straps 30. 32.

FIGS. 19–22 illustrate an alternative embodiment of the invention. having a single releasable strap 60 which forms both first and second stabilizing straps 60a, 60b. In this embodiment. a boot-like body member 62 like that of the previous embodiment is provided. and strap 60 is provided with a fastener 64a of a mating fastener pair, with the mating fastener (not shown) being provided on the rear of the body member. The first stabilizing strap 60a desirably includes a first fastener 66a with a mating fastener 66b being provided on the corresponding side of the body member 62, in the same manner as fasteners 36a and 36b are described with respect to the embodiment of the invention shown in FIG. 2. The second stabilizing strap likewise includes a first fastener 68a, which is adapted to releasably secure to fastener 68b, located on the corresponding side of the body member 62. In this way, the straps 60a, 60b can be wrapped around a wearer's foot in the same manner as that described above with respect to the FIGS. 14–18. In a preferred form of the invention, the fasteners 66a, 66b, 68a, 68b are of the hook and loop variety.

The boot-like body member 62 desirably includes a first fastener 70a of a third fastener pair positioned proximate the calcaneus of a wearer's foot. which is adapted to mate with fastener 70b, which is located on one of the stabilizing straps 60a, 60b. (Although the fastener is illustrated as being on strap 60a, it is noted that it can likewise be located on strap 60b; it is desirable that it be located on the strap to be wrapped around the foot first. in order that it can mate with fastener 70a.) The fastener pair 70a, 70b is desirably of the unidirectional hook and loop variety. In this way, the strap, after being secured about a wearer's foot in the manner described above with respect to the other embodiments of the invention, can be cinched tighter without having to be first fully released. In a particularly preferred form of the invention, the fastener 70a secured to the body member is of a pile variety, while the fastener 70b includes a plurality of hooks which are curved in a common direction. In this way, the strap 60 can be removed from the body member 62 and rotated 180°, so that the third fastener pair 70a, 70b can be selectively utilized to secure the inner or the outer strap, or so that the device can be used to selectively fit either of a wearer's feet. The strap 60 can also include auxiliary fasteners 72a, 72b, which are adapted to provide additional securement for the fasteners 66a, 68a, in the manner described above with respect to the other embodiments of the invention. Loops L can also be provided proximate one or both of the strap ends, in order to aid in the securement and cinching of the stabilizing straps when the device is worn.

The fact that the stabilizing straps are attached at or near a rear portion of the ankle portion at an elevation above the malleoli of the wearer is seen to provide desirable leverage for effectively restraining inversion and eversion of the ankle, while permitting both flexion and dorsiflexion of the wearer's foot. Further, because relative motion between the body member 12 and at least one of the stabilizing straps is effectively obviated due to the third pair of fasteners, the stabilizing forces can be more effectively concentrated proximate the wearer's calcaneus. Further, the malleoli pads assist in supporting the ankle portion in position, by abutting the malleoli of the wearer and preventing it from moving downwardly toward the foot in response to the pressures of the stabilizing straps. As a result, extremely effective restriction against inversion and eversion can be obtained, while flexion and dorsiflexion are not undesirably affected.

As a further important feature of the appliance, it will be understood that the appliance is adapted to be readily re-tightened while on the wearer's foot, by releasing the binding strap(s) and pulling up on the free ends of the two stabilizing straps to disengage the first and second fastener pairs. The first secured strap (i.e., the one with the centrally located unidirectional fastener) can be tightened while the unidirectional fastener elements are still secured together.

Although a preferred embodiment of the invention has been disclosed for illustrative purposes, it is not limited to the specific forms or arrangements of parts herein described and shown, the invention being set forth in the claims listed below.

That which is claimed is:

1. An ankle stabilizing appliance comprising:

a substantially non-elastic boot-like body member configured to receive ankle and rear foot portions of a wearer therein, said body member including an ankle portion adapted to overlie sides and a rear of the ankle of the wearer with said ankle portion having a length sufficient to extend above the malleoli of the wearer, a foot portion configured to extend under at least a portion of the foot of the wearer, and opposing laterally spaced apart front edges extending along at least a portion of said ankle portion, and with said ankle portion defining an inside panel corresponding to the inside of the ankle, an outside panel corresponding to the outside of the ankle, and a rear portion which extends vertically between the inside and outside panels and thus along the Achilles tendon region of the wearer, when in use a connector for drawing said front edges of said body member toward each other so as to permit said body member to be secured about the ankle and rear portion of the foot of the wearer, a pair of elongate substantially non-elastic stabilizing straps, with said straps each having a first end operatively associated with a rear portion of said ankle portion to define an inside strap extending toward said inside panel and an outside strap extending toward said outside panel, a first pair of mating fasteners attached respectively to said inside panel of said ankle portion and to a free end of said inside strap, and a second pair of mating fasteners attached respectively to said outside panel of said ankle portion and to a free end of said outside strap, a first fastener of a mating unidirectional fastener pair secured on a bottom portion of said body member and adapted to correspond to the calcaneus of a wearer's foot, when in use and a second fastener of a unidirectional fastener pair positioned on a central region of one of said stabilizing straps, such that when that stabilizing strap is brought across the top of a wearer's foot, downwardly and underneath the foot, and then upwardly again such that said free end thereof is releasably attached to said ankle portion, said mating unidirectional fastener pair is secured together such that it restricts lateral relative movement between the stabilizing strap and the bottom portion of the body member in substantially all but one direction.

2. An ankle stabilizing appliance according to claim 1, wherein said mating unidirectional fastener pair comprises a unidirectional hook and loop fastener pair.

3. An ankle stabilizing appliance according to claim 2, wherein said first fastener of said unidirectional fastener pair comprises a plurality of hook elements, substantially all of which are curved in a common direction.

4. An ankle stabilizing appliance according to claim 3, wherein substantially all of said hook elements are curved in a direction toward the panel of the ankle portion to which the free end of the strap is to be releasably attached.

5. An ankle stabilizing appliance according to claim 4, wherein said second fastener of said mating unidirectional fastener pair is secured to said outside strap.

6. An ankle stabilizing appliance according to claim 4, wherein said second fastener of said mating unidirectional fastener pair is secured to said inside strap.

7. An ankle stabilizing appliance according to claim 1, further comprising a malleolus pad secured on each of said inside and outside panels and configured to extend substantially above the malleoli of the wearer's foot in an abutting relationship therewith.

8. An ankle stabilizing appliance according to claim 7, wherein said malleoli pads are asymmetrical, to substantially correspond to the differential shaping of the inside and outside malleoli.

9. An ankle stabilizing appliance according to claim 8, wherein one of said malleoli pads is relatively thicker and taller than the other of said pads.

10. An ankle stabilizing appliance according to claim 1, further comprising a binding strap secured to said ankle portion and including a pair of mating fasteners for securing said binding strap about a wearer's ankle, such that when each of said inside and outside stabilizing straps is brought across the top of a wearer's foot, downwardly underneath the foot, and upwardly again such that the free ends are secured to the respective inside and outside panels by way of securing together of the first and second pairs of mating fasteners, said binding strap can be secured circumferentially about the ankle in an overlying relationship to said stabilizing straps.

11. An ankle stabilizing appliance according to claim 1, wherein the second fastener of the unidirectional fastener pair is secured to a first of said pair of stabilizing straps, and further comprising an additional pair of mating fasteners attached respectively to the side of said first stabilizing strap opposite that including the unidirectional fastener and the second stabilizing strap, such that when said second stabilizing strap is brought across the top of a wearer's foot, downwardly and underneath the foot, and then upwardly again such that the free end thereof is releasably attached to the ankle portion, the additional pair of mating fasteners is releasably attached together in a stacked relationship with said attached mating unidirectional fastener pair.

12. An ankle stabilizing appliance according to claim 1, wherein said pair of elongate substantially non-elastic stabilizing straps are formed from a single substantially continuous piece of material, and the single substantially continuous piece of material is releasably secured to the ankle portion of said body member.

13. An ankle stabilizing appliance comprising:

a substantially non-elastic boot-like body member configured to receive ankle and rear foot portions of a wearer therein, said body member including an ankle portion defined by an inside panel for covering the inside malleolus of a wearer's ankle and an outside panel defined by an outside panel for covering the outside malleolus of a wearer when in use, and a connector for connecting said inside panel to said outside panel and thereby securing the body member about a wearer's foot, a pair of elongate substantially non-elastic stabilizing straps, with said straps each having a first end operatively associated with a rear portion of said ankle portion to define an inside strap extending toward said inside panel and an outside strap extending toward said outside panel, a first pair of mating fasteners attached respectively to said inside panel of said ankle portion and to a free end of said inside strap, and a second pair of mating fasteners attached respectively to said outside panel of said ankle portion and to a free end of said outside strap, wherein said inside strap may be brought across the inside panel of said ankle portion, over the top of the wearer's foot, downwardly across the outside of the wearer's foot, under the wearer's foot and then upwardly so that said free end thereof is attached to said ankle portion by securement of said first pair of mating fasteners, and said outside strap may be brought across the outside panel of said ankle portion, over the top of the wearer's foot, under the wearer's foot, and then upwardly so that said free end thereof is attached to said ankle portion by securement of said second pair of mating fasteners, to thereby assume an operative position, and an inside malleolus pad positionable on said inside panel so as to extend substantially above the inside malleolus in an abutting relationship therewith when the appliance is properly positioned a wearer, and an outside malleolus pad positionable on said outside panel so as to extend substantially above said outside malleolus in an abutting relationship therewith when the appliance is properly positioned on a wearer, wherein said inside and outside malleoli pads are asymmetrical to substantially conform to the respective differential shaping of the inside and outside malleoli, and are adapted to support said inside and outside panels against a tendency to collapse downwardly when said stabilizing so straps are in the operative position.

14. An ankle stabilizing appliance according to claim 13, wherein each of said malleoli pads are substantially eyebrow-shaped, and said outside malleolus pad is relatively thicker and taller than said inside malleolus pad.

15. An ankle stabilizing appliance according to claim 13, further comprising a first fastener of a mating unidirectional fastener pair positioned on a bottom portion of said body member and adapted to correspond to the calcaneus of a wearer's foot, and a second fastener of a unidirectional fastener pair positioned on a central region of one of said stabilizing straps, such that when that stabilizing strap is brought across the top of a wearer's foot, downwardly and underneath the foot, and then upwardly again such that said free end thereof is releasably attached to said ankle portion, said mating unidirectional fastener pair is secured together such that it restricts lateral relative movement between the stabilizing strap and the bottom portion of the body member in substantially all but one direction.

16. An ankle stabilizing appliance according to claim 15, wherein said one fastener of said unidirectional fastener pair comprises a plurality of hook elements substantially all of which are curved in a common direction.

17. An ankle stabilizing appliance according to claim 15, wherein said second fastener of said unidirectional fastener pair is positioned on a central region of said outside strap, and said first fastener positioned on the bottom portion of said body member comprises a plurality of hook elements, substantially all of which are curved toward said outside panel of said ankle portion.

18. An ankle stabilizing appliance according to claim 15, wherein said second fastener of said unidirectional fastener pair is positioned on a central region of said inside strap, and said first fastener positioned on the bottom portion of said body member comprises a plurality of hook elements, substantially all of which are curved toward said inside panel of said ankle portion.

19. An ankle stabilizing appliance according to claim 15, wherein said pair of elongate substantially non-elastic stabilizing straps are formed from a single substantially continuous piece of material, and said substantially continuous piece of material is releasably attached to said boot-like body member, such that said piece of material can be rotated so that the portion including said second fastener of a unidirectional fastener pair is selectively positioned to form the inside strap or the outside strap on each of the left and right feet of a wearer.

20. An ankle stabilizing appliance according to claim 13, wherein said inside and outside panels of said boot-like body member include a pair of symmetrical pockets thereon, with the inside and outside malleolus pads being selectively positionable within said respective symmetrical pockets such that a wearer can interchange said inside malleolus pad and outside malleolus pad to determine whether an appliance is adapted to be worn on the left foot or the right foot.

21. An ankle stabilizing appliance comprising:

a substantially non-elastic boot-like body member configured to receive ankle and rear foot portions of a wearer therein, said body member including an ankle portion defined by an inside panel for covering the inside malleolus of a wearer's ankle and an outside panel defined by an outside panel for covering the outside malleolus of a wearer, a connector for connecting said inside panel to said outside panel and thereby securing the body member about a wearer's foot and ankle, when in use and a foot portion for covering at least a bottom portion of the calcaneus of the wearer's foot, a substantially non-elastic inside stabilizing strap, said strap having a first fixed end operatively associated with a rear portion of said ankle portion such that said inside stabilizing strap extends toward said inside panel, and a second free end, a first pair of mating fasteners attached respectively to said inside panel of said ankle portion and to said free end of said inside stabilizing strap, a substantially non-elastic outside stabilizing strap, said strap having a first fixed end operatively associated with a rear portion of said ankle portion such that said outside stabilizing strap extends toward said outside panel, and a second free end, a second pair of mating fasteners attached respectively to said outside panel of said ankle portion and to said free end of said outside stabilizing strap, and a third pair of mating fasteners, said fasteners being adapted to restrict lateral relative motion in substantially all but a single direction, said fasteners being attached respectively to an underside of said foot portion proximate the calcaneus of a wearer's foot and a central portion of one of said inside and outside stabilizing straps, whereby when the strap having the third fastener thereon is brought across the top of a wearer's foot, downwardly and underneath the foot, and then upwardly again such that the fastener on said free end thereof is releasably attached to the fastener on said ankle portion, said third fastener pair is secured together such that all relative lateral movement of the third fastener pair is restricted except for that in the direction in which the strap is wrapped.

22. An ankle stabilizing appliance according to claim 21, further comprising a malleolus pad positioned on each of said inside and outside panels, said malleoli pads being configured to extend substantially above the malleoli of the wearer's foot in an abutting relationship therewith such that said malleolus pads support said inside and outside panels against downward motion with respect to the wearer's foot.

23. An ankle stabilizing appliance according to claim 21, wherein said third pair of mating fasteners comprises a first fastener including a plurality of hooks thereon, substantially all of which are curved in a common direction, and a second fastener having a plurality of filament loops contained thereon and adapted for tangling engagement with said first fastener.

24. An ankle stabilizing appliance according to claim 21, further comprising a binding strap secured to said ankle portion and including a fourth pair of mating fasteners for securing said binding strap about a wearer's ankle, such that when each of said inside and outside stabilizing straps is brought across the top of a wearer's foot, downwardly underneath the foot, and upwardly again such that the free ends are secured to the respective inside and outside panels by way of securing together of the first and second pairs of mating fasteners, said binding strap can be secured circumferentially about the ankle in an overlying relationship to said stabilizing straps.

* * * * *

UNITED STATES PATENT AND TRADEMARK OFFICE
CERTIFICATE OF CORRECTION

PATENT NO. : 5,795,316
DATED : August 18, 1998
INVENTOR(S) : Gaylord It is certified that error appears in the above-identified patent and that said Letters Patent is hereby corrected as shown below:

Column 13, line 34, after wearer, delete ","; after use, insert --,--.

Column 13, line 54, after foot, delete ","; after use, insert --,--.

Column 15, line 28, after positioned, insert --on--; line 37, delete "so".

Column 16, line 40, after ankle, delete ",", after use, insert --,--.

Signed and Sealed this

First Day of December, 1998

*Attest:*

BRUCE LEHMAN

*Attesting Officer*　　*Commissioner of Patents and Trademarks*